United States Patent [19]
Gautier et al.

[11] Patent Number: 6,143,778
[45] Date of Patent: Nov. 7, 2000

[54] PHARMACEUTICAL AMIODARONE COMPOSITION FOR PARENTERAL DELIVERY

[75] Inventors: Jean-Claude Gautier, Clapiers; Regine Bellamy, Restinclieres, both of France

[73] Assignee: Sanofi, Paris, France

[21] Appl. No.: 08/981,634

[22] PCT Filed: Jun. 28, 1996

[86] PCT No.: PCT/FR96/01010

§ 371 Date: Mar. 13, 1998

§ 102(e) Date: Mar. 13, 1998

[87] PCT Pub. No.: WO97/02031

PCT Pub. Date: Jan. 23, 1997

[30] Foreign Application Priority Data

Jun. 30, 1995 [FR] France ................................. 95 07939

[51] Int. Cl.⁷ ................................................. A61K 31/343
[52] U.S. Cl. ................................................................ 514/469
[58] Field of Search .............................................. 514/469

[56] References Cited

FOREIGN PATENT DOCUMENTS 93 19753  10/1993  WIPO .

OTHER PUBLICATIONS

Gough et al., J. Cardiovasc. Pharamacol. (1982), 4(3), 375–80 (Abstract).
Ward et al., J. Parenter. Sci. Technol. (1993), 47(4), 161–5 (Abstract).

*Primary Examiner*—Phyllis G. Spivack
*Attorney, Agent, or Firm*—Jacobson, Price, Holman & Stern, PLLC

[57] ABSTRACT

The invention relates to a pharmaceutical composition for parenteral administration, characterized in that it comprises:
  from 1.5 to 8% by weight of an active principle consisting of amiodarone or one of the pharmaceutically acceptable salts thereof
  a physiologically acceptable buffer solution capable of solubilizing the active principle and of maintaining the pH of the composition between 2.4 and 3.8
  a nonionic hydrophilic surfactant.

30 Claims, No Drawings

PHARMACEUTICAL AMIODARONE COMPOSITION FOR PARENTERAL DELIVERY

The application is a 371 of PCT/FR96/01010, filed Jun. 28, 1996.

The present invention relates generally to a novel pharmaceutical composition containing a substituted benzoyl-benzofuran as active principle.

In particular, the invention relates to a pharmaceutical composition for parenteral administration containing, as active principle, 2-n-butyl-3-[3,5-diiodo-4-(2-diethylaminoethoxy)benzoyl]benzofuran, also known as amiodarone, or one of the pharmaceutically acceptable salts thereof, preferably its hydrochloride.

This compound, known for its beneficial properties on the cardiovascular system, is currently widely used, in the form of its hydrochloride, as an antiarrhythmic agent and as an active principle in the fundamental treatment of coronary insufficiency.

It is available in particular in the form of a solution for parenteral administration, that is to say in the form of a concentrated injectable solution, which can be diluted down to a solution for administration by perfusion.

However, on account of its intrinsic solubility, amiodarone hydrochloride poses certain problems in the development of an injectable pharmaceutical formulation which is at the same time concentrated, stable and dilutable.

Indeed, it has been observed that the solubility of this salt in water depends highly on the temperature: at 20° C. the solubility is from 0.3 to 0.5 mg/ml, whereas under hot conditions, at about 60° C., it increases abruptly to in excess of 100 mg/ml.

In addition, the study of light scattering of an aqueous solution containing 50 mg/ml of this active principle shows appreciable degrees of scatter which tend to prove that, even at high concentration, colloidal structures exist, measurements of the diameters by photon correlation moreover revealing a population centred around 100 nm.

Similarly, observation of concentrated aqueous solutions of amiodarone hydrochloride phase using contrast microscopy allows a smectic-type supramolecular organization to be distinguished.

Following these observations, the theory was put forward that this solubilized active principle has a micellar, or rather bicontinuous, structure.

This aqueous "pseudo-solution" obtained by heating is fairly stable. However, if it is diluted in water, it suddenly becomes turbid below 2 mg/ml.

Study of such dilute solutions by light scattering shows, in point of fact, the sudden appearance of vesicle-type structures of large diameter (about 10,000 nm), which are responsible for the turbidity below that concentration.

During dilution, it consequently appears to be desirable to maintain this apparently supramolecular structure of bicontinuous type, which corresponds to a state of equilibrium.

Amiodarone hydrochloride, in the form of a concentrated solution (50 mg/ml) is currently marketed in 3 ml ampoules, in particular for direct injectable administration. For use in perfusion, the content of this ampoule, which corresponds to the following formulation (% by weight/volume):

| | |
|---|---|
| Amiodarone hydrochloride | 5% |
| Polysorbate 80 | 10% |
| Benzyl alcohol | 2% |
| Water for injectable preparation | 83% | must be added to a reduced volume, in this case 250 ml, of a glucose saline solution, so as to reach quickly and to maintain a therapeutic blood level.

Parenteral solutions with concentrations of less than 2 mg/ml, in particular solutions of from 0.5 to 2 mg/ml, are generally made up by dilution of injectable solutions containing 50 mg/ml of amiodarone hydrochloride as indicated above.

Thus, the administration of amiodarone hydrochloride according to this injectable formulation uses an aqueous solution of this active principle containing 100 times its solubility limit in water at room temperature. Moreover, for an administration by perfusion, the formulation in question must be diluted such that the concentration of active principle after dilution is within the very region of maximum instability of approximately between 0.5 mg/ml and 2 mg/ml, which consequently justifies the presence of a relatively high content of polysorbate 80 as stabilizer.

However, it is well known that polysorbate 80, especially at non-negligible concentrations, can to a certain extent cause undesirable physiological effects.

It is thus important to be able to have available an aqueous solution of amiodarone, for example in the form of its hydrochloride, which is both concentrated and devoid of the above drawbacks, or a solution for which the incidence of the drawbacks has been greatly reduced, while at the same time being dilutable to therapeutically useful concentrations.

An attempt has already been made to overcome these drawbacks, although only partial solutions to the problems posed have been provided.

For example, international patent application Wo 93/19753 has proposed concentrated amiodarone compositions for parenteral administration, that is to say injectable solutions, prepared under hot conditions and then cooled, containing from 15 to 50 mg/ml of active principle, more particularly from 25 to 50 mg/ml solutions, in an aqueous acetate buffer system which maintains the pH at from 3.2 to 4.6, more generally at from 3.2 to 3.8.

It was also mentioned therein that in a phthalate buffer (0.1M; pH=3.5 to 3.8), a precipitate forms when the heated amiodarone solution is cooled, whereas a gel forms at all pHs on cooling a solution of this active principle preheated in a phosphate buffer (0.1M; pH=3.5 to 3.8).

The above patent application also gives examples of dilute solutions for administration by perfusion, containing from 0.10 to 0.15 mg/ml of amiodarone. However, these dilute solutions were prepared not from concentrated solutions, such as the 25 to 50 mg/ml solutions given as examples, but from a stock solution containing from 10 to 15 mg/ml of active principle in an acetate buffer of pH=3.8, introduced into a saline/dextrose solution.

In practice, for a parenteral treatment, two different stock solutions are consequently necessary, one concentrated for administration by direct injection, the other relatively non-concentrated for dilution to a solution for administration by venous perfusion.

Furthermore, the dilute solutions for parenteral administration thus obtained have major drawbacks which make them difficult or even unacceptable to use therapeutically. Indeed, given the daily dosage recommended for an administration of amiodarone hydrochloride by venous perfusion, namely from 5 to 20 mg/kg/day and their high rate of dilution, the solutions given in the examples in the above patent application, containing from 0.10 to 0.15 mg/ml of active principle, should be administered in extremely large volumes, on average from 4 to 5 liters per day, which is entirely out of the question in medical practice.

Preliminary studies carried out in the context of the present invention have clearly shown the limits of the concentrated or dilute parenteral solutions proposed in the abovementioned patent application.

For example, it has been possible to demonstrate that concentrated solutions of amiodarone hydrochloride, such as 15 to 50 mg/ml solutions in an acetate buffer with a pH of between 3.2 and 3.8, cannot be diluted in glucose-saline water beyond 1 mg/ml without forming very opalescent or even milky solutions.

On the other hand, although 10 to 15 mg/ml solutions of this active principle can be highly diluted in glucose-saline water down to 0.10 to 0.15 mg/ml, it is still not possible to effect dilution in the particularly critical concentration zone of 0.5 to 0.8 mg/ml without the appearance of strong turbidity.

Lastly, these concentrated solutions, prepared under hot conditions, require that a very precise temperature be observed, namely 61° C.±1° C., otherwise there is a risk of pronounced turbidity appearing and non-reproducible compositions being formed.

These results together explain both the duality of the stock solutions required for a parenteral administration, according to the above patent application, as well as the particularly high dilution of the compositions for administration by perfusion proposed in this same patent application.

The search for a concentrated injectable formulation of amiodarone, preferably in the form of one of the pharmaceutically acceptable salts thereof such as its hydrochloride, which is both dilutable to therapeutically acceptable concentrations and devoid of the drawbacks reported above, consequently remains of unquestionable interest.

It has now been discovered according to the invention, surprisingly, that it is actually possible to obtain concentrated aqueous solutions of amiodarone, in particular in the form of its hydrochloride, preferably solutions of from 30 to 50 mg/ml or 3 to 5% by weight, which can be used both in direct injection or by perfusion after appropriate dilution, for example in a glucose saline solution.

Thus, it has been possible to demonstrate that the addition of a sufficient amount of a surfactant to a solution of amiodarone, preferably in the form of a pharmaceutically acceptable salt such as the hydrochloride, in an appropriate buffer solution makes it possible to form clear, stable, concentrated solutions of active principle which can be diluted, if necessary, down to the critical zone of 0.5 to 2 mg/ml or 0.05 to 0.2% by weight in order to form a pharmaceutical composition for administration by perfusion.

Consequently, the invention relates to a pharmaceutical composition for parenteral administration, comprising:
  from 1.5 to 8% relative to the weight of the final composition, preferably from 3 to 5%, of active principle consisting of amiodarone or one of the pharmaceutically acceptable salts thereof, in particular its hydrochloride
  a physiologically acceptable buffer solution capable of maintaining the pH of the composition between 2.4 and 3.8
  a nonionic hydrophilic surfactant.

In the rest of the description and likewise in the claims, and except where otherwise mentioned, the percentages of the various constituents forming the compositions of the invention, namely the active principle, the buffer medium and the surfactant, all express weight proportions, namely % relative to the weight of the final composition, whether this be concentrated or dilute.

In general, the buffer solution is chosen from physiologically acceptable aqueous solutions capable both of dissolving the active principle and of maintaining the pH of the compositions between 2.4 and 3.8, preferably between 3.2 and 3.8.

Indeed, although pH values below 2.4 cannot be tolerated by the patient, pH values above 3.8 prove to be incompatible, since instability of the concentrated compositions of active principle, in particular of amiodarone hydrochoride, are recorded thereat, even in the presence of a nonionic hydrophilic surfactant, this being reflected in pronounced turbidity and even in the formation of gel.

Thus, buffer systems which can be used in the context of the invention may be, for example, an aqueous solution of acetic acid/alkali metal acetate, such as sodium acetate or potassium acetate, which is capable of stabilizing the pH at about 3.5, an aqueous solution of Mac Ilvaine buffer, comprising a phosphoric acid/monopotassium phosphate/citric acid combination, capable of effecting a worthwhile stabilization of the pH at from 2.4 to 3.3, or alternatively an aqueous solution of orthophosphoric acid/monoalkali metal phosphate, for example monosodium phosphate or monopotassium phosphate or an aqueous solution of glycine/strong acid such as hydrochloric acid, it being possible for these buffer solutions to maintain the pH effectively at about 3.3.

In most cases, the ionic strength of the buffer solution will be between 0.08 molar and 0.3 molar, preferably between 0.1 and 0.3 molar, depending on the buffer system chosen. Beyond 0.3 molar, the salt concentration in the medium runs the risk of disrupting the stability of the compositions of the invention and of resulting in hypertonicity of the formulations; whereas at a concentration below 0.08 molar, the buffer effect becomes inexistent.

By way of example, mention may be made of aqueous buffer solutions 0.1 to 0.15 molar with respect to orthophosphoric acid/monoalkali metal phosphate, for example monosodium phosphate or monopotassium phosphate; 0.1 to 0.3 molar with respect to acetic acid/alkali metal acetate, for example sodium acetate or potassium acetate, or 0.2 molar with respect to glycine/strong acid such as hydrochloric acid.

On the other hand, buffers such as citric acid/sodium citrate or potassium hydrogen phthalate, although capable of maintaining the pH in the required zone, proved to be unsuitable even in the presence of a surfactant according to the invention, the active principle not being soluble in these buffer solutions.

As regards the surfactant, it is generally chosen from nonionic hydrophilic compounds whose hydrophilic/lipophilic balance, commonly defined as its "HLB" value which reflects the proportion of hydrophilic groups and of lipophilic groups in the molecule according to the system by Griffin W. C. [J. Soc. Cosm. Chem, 1, 311 (1949)], is between 13 and 29; preferably between 13 and 17.

In general, this nonionic hydrophilic surfactant is incorporated into the parenteral compositions of the invention at an amount of from 0.5% to 2%, preferably at a concentration of from 0.9 to 1.5%.

Surfactants of this type may be, for example, an ethylene oxide/propylene oxide copolymer such as those marketed under the trade names Pluronic® P 94 (HLB: 13.5) and Pluronic® F 68 (HLB: 29), a polyethoxylated castor oil such as that marketed under the trade name Cremophor® EL (HLB: 13), an ethoxylated polysorbate such as polysorbate 80 (HLB: 15) marketed under the trade name Tween® 80 or alternatively a polyethylene hydroxystearate such as polyethylene hydroxystearate –660 (HLB: 13) marketed under the trade name Solutol® HS 15.

If necessary, the compositions of the invention may comprise one or more additional ingredients, in particular a preserving or protective agent such as a bactericide.

By way of example, mention may be made of benzyl alcohol in low proportion, that is to say up to 1% relative to the weight of the final composition.

The compositions of the invention thus formed are characterized by a considerable stability, which allows them both to be stored for long periods and used effectively for administration by direct injection.

In this respect, preferred compositions of the invention for administration by injection contain from 3 to 5% of active principle such as amiodarone hydrochloride, a 0.1 molar orthophosphoric acid/sodium monophosphate buffer solution and from 1.3 to 1.6% of polysorbate 80.

The pharmaceutical compositions of the invention may be obtained conventionally by heating, to a temperature of 60° C. to 70° C., a medium formed of a suitable buffer solution, the nonionic hydrophilic surfactant selected and the active principle, and then by cooling the pharmaceutical composition thus formed to room temperature.

This composition of clear appearance may be prepared at any temperature within the range considered, in contrast with the patent application mentioned above in which the very narrow range of 61° C.±1° C. must be rigorously adhered to.

It has also been observed, in the context of the present invention, that, for administration by venous perfusion, the injectable compositions of the invention can be diluted so as to reduce the concentration of active principle down to at least a minimum of 0.05% relative to the weight of the dilute composition without any fear of opalescence occurring.

Consequently, according to another of its aspects, the invention relates to a pharmaceutical composition for parenteral administration, comprising:

from 1.5% to 8%, in particular from 3 to 5%, of an active principle consisting of amiodarone, preferably in the form of one of the pharmaceutically acceptable salts thereof, in particular its hydrochloride a buffer solution and a nonionic hydrophilic surfactant such as the buffer solutions and surfactants described above for the injectable concentrated compositions of the invention, and a sufficient amount of a physiologically acceptable diluent, the total concentration of active principle not being less than 0.05%.

Preferably, the dilute compositions of the invention comprise from 0.05% to 0.5%, usually from 0.08 to 0.2%, of active principle, whereas the physiologically acceptable diluent is generally formed of physiologic saline solution containing a carbohydrate such as, for example, glucose (or dextrose) or sorbitol.

The characteristics and advantages of the compositions according to the invention will become apparent in the light of the description which follows, from compositions given as examples.

I—Determination of the Turbidity of Compositions According to the Invention

The results of various tests carried out in order to determine, by nephelometry, the turbidity of amiodarone hydrochloride solutions according to the invention, which may or may not be diluted in glucose saline, are reported below.

To this end, a laboratory turbidimeter capable of measuring turbidities of between 0.001 and 1999 nephelometric turbidity units (NTU) was used.

The test consisted in directing a light beam, having a wavelength of 550±50 nm, so that it passes right through the solution to be studied.

The light scattered at an angle of 90° C., the light scattered at an angle of 30° C. relative to the direction of the incident light and the light transmitted through the solution are then measured with the aid of detectors.

The results were expressed in NTU and were interpreted as follows:

| Turbidity (T) (in NTU) | The solution is considered to be: |
| --- | --- |
| T < 3 | Clear |
| 3 < T < 6 | Weakly opalescent |
| 6 < T < 18 | Opalescent |
| 18 < T < 30 | Very opalescent | a) Formulation in the Acetic Acid/Sodium Acetate Buffer Medium

The turbidity results of a concentrated solution of amiodarone hydrochloride of following formulation:

Amiodarone hydrochloride 5.00%

Acetic acid/sodium acetate buffer medium (0.1M; pH=3.6) 93.10%

Pluronic® F 68 1.90% were determined after storage for 1 month at various temperatures, namely 5° C., 25° C. and 35° C.

The same determinations were made under the same conditions, starting with an identical solution diluted until a concentration of 0.1% amiodarone hydrochloride in a 5% by weight glucose saline solution was obtained.

In each case, the concentration of active principle at the time of determination of the turbidity was assayed.

The results obtained are given below:

| Storage temperature (° C.) | Concentration of amiodarone hydrochloride (%) | Turbidity (NTU) | pH of the solution |
| --- | --- | --- | --- |
| 5 | 4.998 | 3.4 | 3.52 |
|   | 0.098 | 0.25 | 4.02 |
| 25 | 4.998 | 3.8 | 3.62 |
|   | 0.102 | 0.27 | 4.06 |
| 35 | 4.998 | 4.1 | 3.63 |
|   | 0.099 | 0.4 | 4.1 | b) Formulation in the Orthophosphoric Acid/Monosodium Phosphate Buffer Medium

The turbidity measurements of amiodarone hydrochloride solutions prepared from a concentrated composition of following formulation:

Amiodarone hydrochloride 5.00%

Orthophosphoric acid/monosodium phosphate buffer medium (0.1M; pH=3.3) 93.58%

Polysorbate 80 1.42% diluted until an amiodarone hydrochloride concentration of 0.10%; 0.06% or 0.05% in a 5% by weight glucose saline solution was obtained gave the following results:

| Concentration of amiodarone hydrochloride (%) | Turbidity (NTU) |
| --- | --- |
| 0.10 | 0.31 |
| 0.06 | 0.31 |
| 0.05 | 0.32 |

No impurity was detected in these tests.

Other tests were performed using concentrated solutions of amiodarone hydrochloride of the following formulations in orthophosphoric acid/monosodium phosphate buffer medium after dilution until an amiodarone hydrochloride concentration of 0.05% in a 5% by weight glucose saline solution was obtained:

| | |
| --- | --- |
| Amiodarone hydrochloride | 5.00% |
| Orthophosphoric acid/monsodium phosphate buffer medium (0.1M; pH = 3.3) | 93.58% |
| Associated surfactant: Cremophor ® EL or Solutol ® HS 15 | 1.42% |

In both cases, a turbidity of 0.4 NTU was recorded.

II—Comparative Studies a) Concentrated Amiodarone Hydrochloride Compositions for Direct Injection Comparative studies, performed between concentrated amiodarone hydrochloride compositions according to the state of the art represented by the abovementioned patent application and a composition of the invention, gave the results reported below:

| Concentration of amiodarone hydrochloride (%) | Buffer medium (0.1M) | Surfactant | Turbidity (NTU) |
| --- | --- | --- | --- |
| 1.0 | Acetic acid/sodium acetate (pH = 3.8) | — | 240 |
| 1.5 | Acetic acid/sodium acetate (pH = 3.8) | — | 19 |
| 5.0 | Acetic acid/sodium acetate (pH = 3.5) | Polysorbate 80 (0.95%) | 3.4 |

These results show that the composition of the invention, containing 5% of active principle, has a very low turbidity, in contrast with the prior compositions. As the turbidity generally reflects the presence of large lumps which are capable of creating problems on injection and of resulting in a lack of stability in the solutions to be administered, the compositions of the invention are effectively more advantageous than the compositions of the state of the art.

b) Dilute Amiodarone Hydrochloride Compositions for Venous Perfusion

Comparative tests similar to the above tests were performed using compositions obtained by dilution of concentrated amiodarone hydrochloride solutions respectively in accordance with the state of the art represented by the abovementioned patent application and in accordance with the invention using a 5% by weight glucose saline solution.

The results, determined immediately after dilution, are reported below:

| Concentration of amiodarone hydrochloride before dilution (%) | Buffer medium (0.1M) | Surfactant (%) | Turbidity (NTU) after dilution to: | |
| --- | --- | --- | --- | --- |
| | | | 0.075% | 0.050% |
| 1.0 | Acetic acid/sodium acetate (pH = 3.8) | — | 690 | 450 |
| 1.5 | Acetic acid/sodium acetate (pH = 3.8) | — | 650 | 580 |
| 5.0 | Acetic acid/sodium acetate (pH = 3.8) | — | 670 | 375 |
| 5.0 | Acetic acid/sodium acetate (pH = 3.5) | Polysorbate 80 (0.95%) | 0.50 | 0.66 |

These results show that although the concentrated composition according to the invention can legitimately be diluted in a glucose saline solution to within the zone from 0.050% to 0.075%, when diluted to these same concentrations, the concentrated compositions of the prior art, on the other hand, give rise to solutions which are very opalescent or even milky in appearance.

A comparative study was also carried out employing solutions prepared from concentrated solutions containing 5% of amiodarone hydrochloride, aqueous or buffered solutions, by dilution in a 5% by weight glucose saline solution.

The following results were obtained:

| Buffer medium (0.1M) | Surfactant (%) | Turbidity (NTU) after dilution to: | |
| --- | --- | --- | --- |
| | | 0.075% | 0.050% |
| Acetic acid/sodium acetate (pH = 3.8) | — | 670 | 375 |
| — | Polysorbate 80 (0.95%) | 360 | 245 |
| — | Polysorbate 80 (1.9%) | 190 | 139 |
| Acetic acid/sodium acetate (pH = 3.5) | Polysorbate 80 (0.95%) | 0.50 | 0.66 |

Thus, it is observed that a concentrated amiodarone hydrochloride solution in the buffer medium alone cannot legitimately be diluted to within the critical zone without very considerable turbidities appearing.

However, a low amount of nonionic surfactant added to this solubilizing buffer medium allows dilution of the concentrated amiodarone hydrochloride solution obtained, whereas this same amount of nonionic surfactant added to an aqueous solution does not allow the concentrated solution thus formed to be diluted.

These results clearly show a synergy effect exerted between the buffer medium and the nonionic surfactant.

By means of this synergy effect demonstrated in buffered medium/nonionic surfactant components, parenteral compositions may be formulated in particular in an orthophosphoric acid/monoalkali metal phosphate medium, in contrast with the state of the art, so as to make up concentrated or dilute active principle concentrations.

The non-limiting examples which follow illustrate the compositions of the invention.

EXAMPLE 1

Injectable Concentrated Amiodarone Hydrochloride Composition

An injectable pharmaceutical composition with a total weight of 100 g and corresponding to the following formulation,

| | |
|---|---|
| Amiodarone hydrochloride | 5 g |
| Orthophosphoric acid/monosodium phosphate buffer medium (0.1M; pH = 3.3) | 93.575 g |
| Polysorbate 80 | 1.425 g | is prepared by application of the process described below:

A 0.1M buffer solution of pH=3.3 is first made up by dissolving 1.56 g of monosodium phosphate (NaH$_2$PO$_4$) in 100 ml of water and then adjusting the pH to 3.3 by addition of molar orthophosphoric acid.

98.5 g of the above buffer solution are then added to 1.5 g of polysorbate 80, followed by addition of 95 g of the medium thus made up to 5 g of amiodarone hydrochloride.

The mixture is then heated on a water bath at between 60 and 70° C. for 15 minutes with stirring, and is then allowed to cool to room temperature.

EXAMPLES 2 TO 14

Injectable Concentrated Amiodarone Hydrochloride Compositions

By following the same method as in Example 1, but varying in particular the nature of the nonionic hydrophilic surfactant, the following compositions, with a total weight of 100 g were prepared:

| | | |
|---|---|---|
| EX. 2 | Amiodarone hydrochloride | 5 g |
| | Acetic acid/sodium acetate buffer medium (0.1M; pH = 3.6) | 93.1 g |
| | Pluronic ® F68 | 1.9 g |
| EX. 3 | Amiodarone hydrochloride | 5 g |
| | Orthophosphoric acid/monosodium phosphate buffer medium (0.1M; pH = 3.3) | 93.575 g |
| | Cremophor ® EL | 1.425 g |
| EX. 4 | Amiodarone hydrochloride | 5 g |
| | Orthophosphoric acid/monosodium phosphate buffer medium (0.1M; pH = 3.3) | 93.575 g |
| | Solutol ® HS 15 | 1.425 g |
| EX. 5 | Amiodarone hydrochloride | 5 g |
| | Orthophosphoric acid/monosodium phosphate buffer medium (0.1M; pH = 3.3) | 93.575 g |
| | Pluronic ® P94 | 1.425 g |
| EX. 6 | Amiodarone hydrochloride | 5 g |
| | Orthophosphoric acid/monosodium phosphate buffer medium (0.15M; pH = 3.3) | 93.575 g |
| | Polysorbate 80 | 1.425 g |
| EX. 7 | Amiodarone hydrochloride | 5 g |
| | Acetic acid/sodium acetate buffer medium (0.3M; pH = 3.5) | 93.575 g |
| | Polysorbate 80 | 1.425 g |
| EX. 8 | Amiodarone hydrochloride | 5 g |
| | Glycine/hydrochloric acid buffer medium (0.2M; pH = 3.3) | 94.05 g |
| | Polysorbate 80 | 0.95 g |
| EX. 9 | Amiodarone hydrochloride | 5 g |
| | Acetic acid/sodium acetate buffer medium (0.1M; pH = 3.5) | 94.05 g |
| | Solutol ® HS 15 | 0.95 g |
| EX. 10 | Amiodarone hydrochloride | 5 g |
| | Acetic acid/sodium acetate buffer medium (0.1M; pH = 3.5) | 94.05 g |
| | Cremophor ® EL | 0.95 g |
| EX. 11 | Amiodarone hydrochloride | 5 g |
| | Acetic acid/sodium acetate buffer medium (0.1M; pH = 3.5) | 93.575 g |
| | Pluronic ® P 94 | 1.425 g |
| EX. 12 | Amiodarone hydrochloride | 5 g |
| | Mac Ilvaine buffer medium (pH = 3.3) | 94.05 g |
| | Polysorbate 80 | 0.95 g |
| EX. 13 | Amiodarone hydrochloride | 5 g |
| | Mac Ilvaine buffer medium (pH = 2.4) | 94.05 g |
| | Polysorbate 80 | 0.95 g |
| EX. 14 | Amiodarone hydrochloride | 1.5 g |
| | Orthophosphoric acid/monosodium phosphate buffer medium (0.1M; pH = 3.3) | 97.0225 g |
| | Polysorbate 80 | 1.4775 g |
| EX. 15 | Amiodarone hydrochloride | 3 g |
| | Orthophosphoric acid/monosodium phosphate buffer medium (0.1M; pH = 3.3) | 95.545 g |
| | Polysorbate 80 | 1.455 g |
| EX. 16 | Amiodarone hydrochloride | 8 g |
| | Acetic acid/sodium acetate buffer medium (0.1M; pH = 3.5) | 90.62 g |
| | Polysorbate 80 | 1.38 g |

EXAMPLE 17

Dosage Unit for Injectable Administration of Amiodarone Hydrochloride 3 ml of a sterilized amiodarone hydrochloride composition as prepared in Example 1 are introduced into a sterilized glass ampoule. The ampoule is then sealed under aseptic conditions so as to make up a dosage unit containing 50 mg/ml of amiodarone hydrochloride or 5% of this active principle.

EXAMPLE 18

Dilute Amiodarone Hydrochloride Composition for Perfusion

A parenteral solution for venous perfusion is prepared by adding 3 ml of an injectable 5% amiodarone hydrochloride composition according to Example 1 or the content of an ampoule according to Example 17 to 250 ml of isotonic injectable glucose solution at a concentration of 5% by weight.

In this way, a perfectly clear parenteral solution containing 0.6 mg/ml of amiodarone hydrochloride or 0.06% of this active principle is made up.

EXAMPLE 19

Dilute Amiodarone Hydrochloride Composition for Perfusion

A parenteral solution for venous perfusion is prepared by introducing 6 ml of an injectable 5% amiodarone hydrochloride composition according to Example 1 or the content of two ampoules according to Example 17 into 250 ml of isotonic injectable glucose solution at a concentration of 5% by weight.

In this way, a perfectly clear parenteral solution containing 1.2 mg/ml of amiodarone hydrochloride or 0.12% of this active principle is obtained.

EXAMPLE 20

Dilute Amiodarone Hydrochloride Composition for Perfusion

Parenteral solutions for venous perfusion containing from 0.5 to 5 mg/ml of amiodarone hydrochloride, i.e. 0.05%. to 0.5% of this active principle, are prepared by introduction of an appropriate volume of an injectable concentrated composition according to Examples 2 to 16 into an isotonic injectable glucose solution at a concentration of 5% by weight.

The parenteral solutions obtained are perfectly clear.

What is claimed is:

1. Pharmaceutical composition for parenteral administration comprising from 1.5 to 8% by weight of an active principle consisting of amiodarone or one of the pharmaceutically acceptable salts thereof which remains stable upon dilution down to a concentration of from 0.05 to 0.2% in active principle, wherein the pharmaceutical composition further comprises:

a physiologically acceptable buffer solution capable of solubilizing the active principle and of maintaining the pH of the composition between 2.4 and 3.8; and from 0.5 to 2% by weight of a nonionic hydrophillic surfactant.

2. Pharmaceutical composition according to claim 1, containing from 3 to 5% of active principle.

3. Pharmaceutical composition according to claim 1, wherein the buffer solution is an aqueous acetic acid/alkali metal acetate solution.

4. Pharmaceutical composition according to claim 3, wherein the acetic acid/alkali metal acetate buffer solution maintains the pH at 3.5.

5. Pharmaceutical composition according to claim 3, wherein the alkali metal is sodium or potassium.

6. Pharmaceutical composition according to claim 1, wherein the buffer solution is an aqueous orthophosphoric acid/monoalkali metal phosphate solution.

7. Pharmaceutical composition according to claim 6, wherein the orthophosphoric acid/monoalkali metal phosphate buffer solution maintains the pH at 3.3.

8. Pharmaceutical composition according to claim 1, wherein the buffer solution is an aqueous Mac Ilvaine buffer solution.

9. Pharmaceutical composition according to claim 8, wherein the Mac Ilvaine buffer solution maintains the pH at 2.4 to 3.3.

10. Pharmaceutical composition according to claim 1, wherein the buffer solution is an aqueous glycine/strong acid solution.

11. Pharmaceutical composition according to claim 10, wherein the glycine/strong acid buffer solution maintains the pH at 3.3.

12. Pharmaceutical composition according to claim 10, wherein the strong acid is hydrochloric acid.

13. Pharmaceutical composition according to claim 1, wherein the ionic strength of the buffer solution is between 0.08 molar and 0.3 molar.

14. Pharmaceutical composition according to claim 1, wherein the buffer solution is an aqueous 0.1 to 0.3 molar acetic acid/alkali metal acetate solution.

15. Pharmaceutical composition according to claim 1, wherein the buffer solution is an aqueous 0.1 to 0.15 molar orthophosphoric acid/alkali metal monophosphate solution.

16. Pharmaceutical composition according to claim 1, wherein the buffer solution is an aqueous 0.2 molar glycine/strong acid solution.

17. Pharmaceutical composition according to claim 1, wherein the surfactant is chosen from nonionic hydrophillic compounds whose HLB value is between 13 and 29.

18. Pharmaceutical composition according to claim 17, wherein the surfactant is selected from the group consisting of nonionic hydrophillic compounds whose HLB value is between 13 and 17.

19. Pharmaceutical composition according to claim 17, wherein the surfactant is selected from the group consisting of an ethylene oxide/propylene oxide copolymer, a polyethoxylated castor oil, an ethoxylated polysorbate, and a polyethylene hydroxystearate.

20. Pharmaceutical composition according to claim 19, wherein the surfactant is selected from the group consisting of commercial products bearing the following trade names: Pluronic® F68, Pluronic® P 94, Cremophor® EL, Tween® 80 and Solutol® HS 15.

21. Pharmaceutical composition according to claim 19, wherein the preserving or protective agent is benzyl alcohol.

22. Pharmaceutical composition according to claim 1, further containing a preserving or protective agent.

23. Pharmaceutical composition for parenteral administration, comprising a composition according to claim 1 and a sufficient amount of a physiologically acceptable diluent, the final concentration of active principle not being less than 0.05% relative to the weight of the dilute composition.

24. Pharmaceutical composition according to claim 23, wherein final concentration of active principle is between 0.05% and 0.5% relative to the weight of the dilute composition.

25. Pharmaceutical composition according to claim 23, wherein the physiologically acceptable diluent is formed of a physiologic saline solution containing a carbohydrate.

26. Pharmaceutical composition according to claim 25, wherein the carbohydrate is glucose.

27. Pharmaceutical composition according to claim 1, wherein the active principle is amiodarone hydrochloride.

28. Pharmaceutical composition for parenteral administration according to claim 1, comprising from 3 to 5% by weight of amiordarone hydrochloride, a 0.1 molar orthophosphoric acid/sodium monophosphate buffer solution, and from 1.3 to 1.6% by weight of Polysorbate 80.

29. Pharmaceutical composition for parenteral administration, comprising a composition according to claim 28 and an effective amount of a physiologic glucose saline solution, the final concentration of amiodarone hydrochloride being not less than 0.05% relative to the weight of the dilute composition.

30. Pharmaceutical composition according to claim 29, containing from 0.05 to 0.5% by weight of amiodarone hydrochloride.

* * * * *